(12) United States Patent
Filippi et al.

(10) Patent No.: US 6,426,054 B1
(45) Date of Patent: *Jul. 30, 2002

(54) REFORMING APPARATUS

(75) Inventors: Ermanno Filippi, Viganello (CH); Enrico Rizzi, Grandate (IT)

(73) Assignee: Amonia Casale S.A., Lugano-Besso (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,237

(22) Filed: Oct. 30, 1997

(30) Foreign Application Priority Data

Dec. 11, 1996 (EP) .............................. 96118105

(51) Int. Cl.[7] .................................. F28D 7/00
(52) U.S. Cl. .................. 422/201; 422/200; 422/202; 422/203; 422/204
(58) Field of Search ............... 422/197, 198, 422/200, 201, 202, 205; 277/436, 570, 931

(56) References Cited

U.S. PATENT DOCUMENTS

| | | | |
|---|---|---|---|
| 2,329,658 A | 9/1943 | Simpson et al. ............ 208/146 |
| 4,113,441 A | 9/1978 | Suzuki et al. ............... 422/197 |
| 4,281,510 A | * 8/1981 | Borjesgard et al. ......... 60/39.32 |
| 4,897,246 A | * 1/1990 | Peterson ................... 422/186.3 |
| 4,907,643 A | 3/1990 | Grotz et al. ............. 165/134.1 |
| 4,921,680 A | 5/1990 | Bonk et al. |
| 5,392,692 A | * 2/1995 | Rao et al. ..................... 92/246 |
| 5,855,112 A | * 1/1999 | Bannai et al. ........... 60/39.511 |

FOREIGN PATENT DOCUMENTS

| | | |
|---|---|---|
| DE | 1085140 | 7/1960 |
| DE | 35 32 413 C2 | 2/1990 |
| EP | 0450872 | 10/1991 |
| JP | 4-154602 | 5/1992 |

OTHER PUBLICATIONS

*Patent Abstracts of Japan*, vol. 016, No. 443 (C–0985), Sep. 16, 1992.
A. S. Foust et al., *Principles of Unit Operations* 1980, Wiley and Sons, New York, USA XP002028737 pp. 327–332.

* cited by examiner

Primary Examiner—Jerry D. Johnson
Assistant Examiner—Frederick Varcoe
(74) Attorney, Agent, or Firm—Sughrue Mion, PLLC

(57) ABSTRACT

A reforming apparatus of the type including an indirect heat exchange zone for the reforming reaction of a gaseous flow comprising methane and steam into CO, $CO_2$ and $H_2$, is provided with a plurality of floating-head tubes containing a reforming catalyst, a chamber for collection of the reaction products positioned downstream of the reaction products from the apparatus.

6 Claims, 2 Drawing Sheets

REFORMING APPARATUS

FIELD OF APPLICATION

The present invention relates to a reforming apparatus of the type comprising an indirect heat exchange zone for the reforming reaction of a gaseous flow comprising methane and steam into CO, $CO_2$ and $H_2$.

In the description given below and in the following claims, the term: "methane" is generally understood to mean a raw material which is a source of hydrogen and carbon such as e.g. methane itself or a mixture of liquid and/or gaseous hydrocarbons such as natural gas and naphtha.

As known, in the field of methane reforming to obtain hydrogen and carbon which are indispensable for the synthesis of products such as ammonia and/or methanol, the requirement to make available an apparatus which on the one hand allows obtaining a reforming reaction of the methane as complete as possible and on the other hand requires low energy consumption and investment and maintenance costs and is easy to implement is ever more pressing.

PRIOR ART

To satisfy the above mentioned requirement, an exchanger-type reforming apparatus, i.e. having a heat exchange zone for the methane reforming reaction, has been proposed in the industry.

In this apparatus, the high quantity of heat necessary for the endothermic reforming reaction is supplied by indirect heat exchange with a flow of heating gas fed to such apparatus.

In particular, in ammonia plants where the methane reforming reaction is performed in two distinct sections called primary and secondary reforming with the latter operating at a higher temperature than the former, it is possible to utilize the hot reacted gas coming from the secondary reforming section as a heat source for the primary reforming section.

The exchanger type reforming apparatus is generally used in the state of the art in ammonia, methane or hydrogen synthesis processes to replace the conventional primary reformer, as described for example in EP-A-0 298 525.

Although advantageous in many ways the above described apparatus displays a series of drawbacks the first of which is being of very complex construction requiring high investment costs.

Indeed, this apparatus comprises in it a plurality of bayonet-type tubes, i.e. consisting of an external tubular element with blind end for indirect heat exchange between the heating gas flow and the gaseous reagents (methane and steam), and an internal tube for extraction of the reaction products.

As may be readily imagined, a structure of this type is complex and costly to construct, difficult to access for maintenance operations, and involves large-diameter reforming apparatus.

In addition, since the reforming reaction is of the catalytic type, it is necessary that the annular space defined between the external tubular element and the internal tube is filled uniformly with catalyst and that the catalyst is replaced periodically. These operations are clearly hindered or at least made difficult by the presence of the internal tube.

Lastly, the use of bayonet-type tubes displays disadvantages even from the energy viewpoint, because there is significant undesired heat exchange between the reacted gas flow and the reacting gas flow, with the added risk of occurrence of metal dusting corrosion of the internal tube due to the reacted gas if the latter is cooled excessively.

JP-A-4154601 describes a reforming apparatus of the exchanger type comprising a plurality of individual tubes filled with catalyst and outside which flows the heating gas.

The tubes are affixed at their ends to respective tube plates which are also appropriately affixed to the reforming apparatus.

Although simpler to construct and operate than the bayonet tubes the heat exchange tubes described in JP-A-4154601 display the serious disadvantage that they are not free to expand if subjected to high temperatures—as in the case of the reforming reaction—with the risk of cracking or even breakage thereof and thus mixing of the reacting gas with the heating gas and damage to the apparatus.

It follows that this type of apparatus not only entails high maintenance costs for replacement of defective tubes, but is not able to ensure optimal and reliable long term operation.

Because of these disadvantages, the exchange-type reforming apparatus according to the prior art has heretofore found little application despite the ever more urgently felt requirement in the industry.

SUMMARY OF THE INVENTION

The problem underlying the present invention is to make available a reforming apparatus which would be simple to implement, reliable, and would provide a methane reforming reaction as complete as possible with low investment, operating and maintenance costs as well as low energy consumption.

The above mentioned problem is solved according to the present invention by a reforming apparatus for the conversion of methane and steam into CO, $CO_2$ and $H_2$ of the type comprising:

a substantially cylindrical external shell in which are defined an indirect heat exchange zone and a zone for feeding a gaseous flow comprising methane and steam to the indirect heat exchange zone;

an opening formed in said shell for feeding in said indirect heat exchange zone a heating gas flow as heat source for said conversion; and which is characterized in that it also comprises:

a plurality of floating-head tubes containing a reforming catalyst, extending longitudinally in said indirect heat exchange zone and in fluid communication with said feeding zone;

a chamber for collecting a gaseous flow comprising CO, $CO_2$, and $H_2$ obtained from said conversion and positioned downstream of said tubes;

a duct open in said collection chamber for extracting from the shell said gaseous flow comprising CO, $CO_2$, and $H_2$.

In the description given below and in the following claims, the term: "floating-head tubes" is understood to mean tubes having at least one end (head) structurally free to move (floating) to allow heat expansion of the tubes.

Advantageously, the reforming apparatus according to the present invention calls for a collection chamber for the reacted gas in fluid communication with a plurality of tubes containing catalyst for indirect heat exchange, and a duct for extraction of this gas from the shell.

In this manner, all the gas—once the reforming reaction has taken place—is collected in the same chamber and extracted by means of a single duct.

Thanks to this particular structure, it is possible to obtain exchange-type reforming apparatus which is reliable, extremely simple to construct and has low implementation costs and which is at the same time effective as regards methane reforming reaction, without the drawbacks typical of the prior art apparatus.

In particular, maintenance operations and loading or replacing the catalyst in the tubes are facilitated by the presence of a plurality of individual floating-head tubes independent of one another.

In addition, since the reacted gas is all collected in a single chamber and extracted from the shell by means of a duct which is thermally independent of the heat exchange tubes, the undesired heat exchange between the reacted gas and the reacting gas is advantageously eliminated to avoid the danger of metal dusting corrosion of the extraction duct and to reduce operating costs as compared with the prior art apparatus.

According to a preferred embodiment of the apparatus in accordance with the present invention, the extraction duct is advantageously arranged coaxially with said shell and extending parallel to said tubes through the indirect heat exchange zone and the feeding zone, from the collection chamber to a gas outlet opening from the shell.

In this manner, there is obtained a very simple and compact structure, permitting at the same time effective compensation for the expansion of the different parts of the apparatus caused by the different thermal stress to which these parts are subject and by the use of different materials.

In particular, it is possible to appropriately and reliably compensate the different expansion rates to which the heat exchange tubes and the reacted gas extraction duct are subjected, without thereby having to give up extremely simple apparatus from the structural point of view.

Indeed, thanks to the special arrangement of the extraction duct there is advantageously obtained a collection chamber which is also of the floating type, with the heat exchange tubes and the extraction duct free to expand in mutually opposite directions with respect to the feeding zone.

In this manner, the different expansion rates of the materials not only do not create mechanical problems for the apparatus but can be mutually compensated in a certain manner.

Advantageously, according to this embodiment, between said duct and a tube plate positioned between said feeding zone and said heat exchange zone as between said duct and said shell, there are provided suitable gas sealing means so as to avoid undesired by-pass of the reaction gas or reacted gas and at the same time to permit the different heat expansion rates of the apparatus.

Thanks to the present invention, the gas sealing means which ensure correct operation of the apparatus are reduced to the minimum and concentrated between the extraction duct, the tube plate and the external shell only.

Preferably, the gas sealing means are arranged near said outlet opening so as to facilitate access to the gas sealing means and thus simplify and aid maintenance thereof.

The characteristics and advantages of the present invention are set forth in the description of an embodiment thereof given below by way of non-limiting example with reference to the annexed drawings.

DETAILED DESCRIPTION OF A PREFERRED EMBODIMENT

Figure 1:
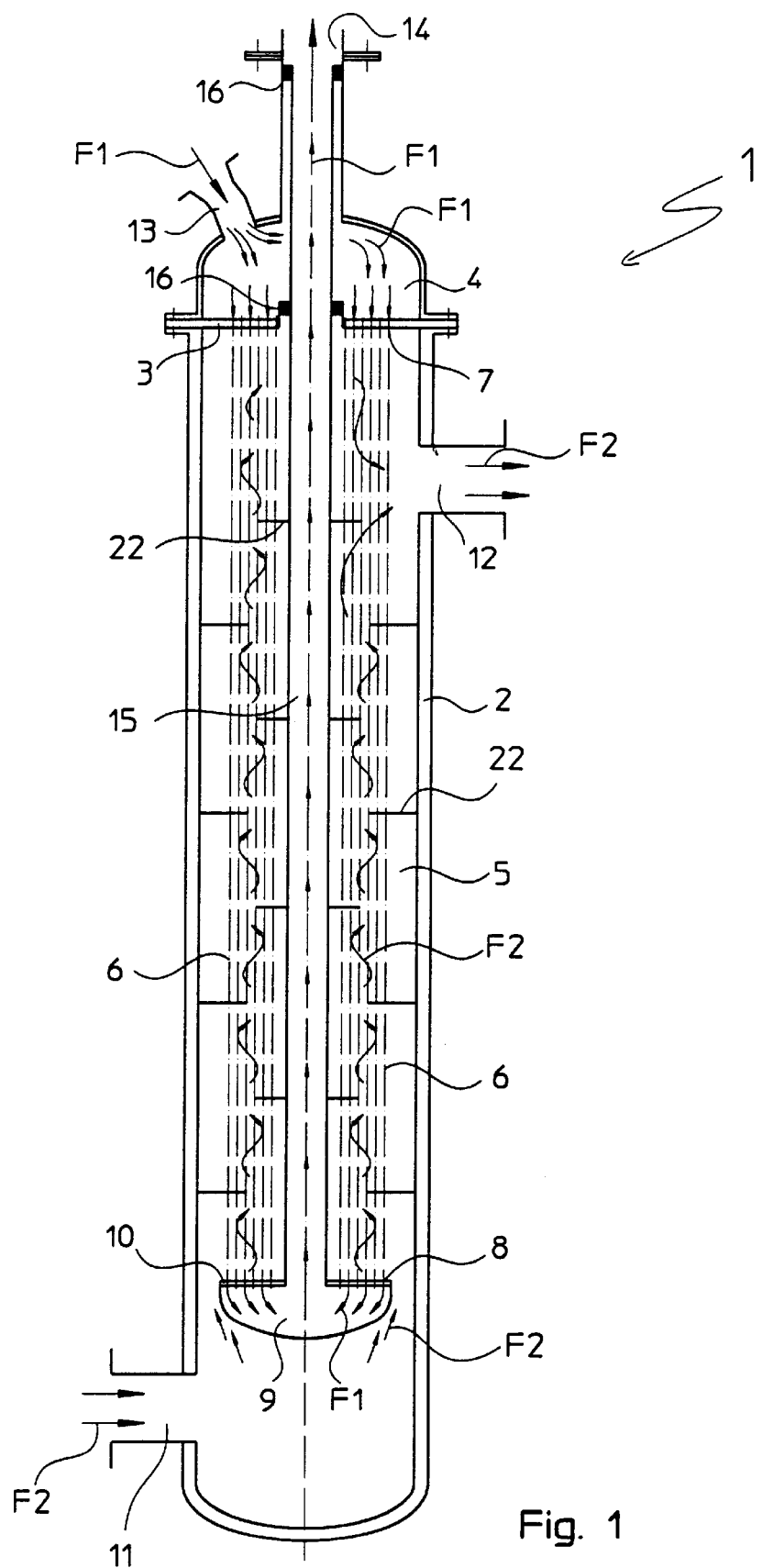
FIG. 1 shows a longitudinal cross section view of a reforming apparatus according to the present invention.
Figure 2:
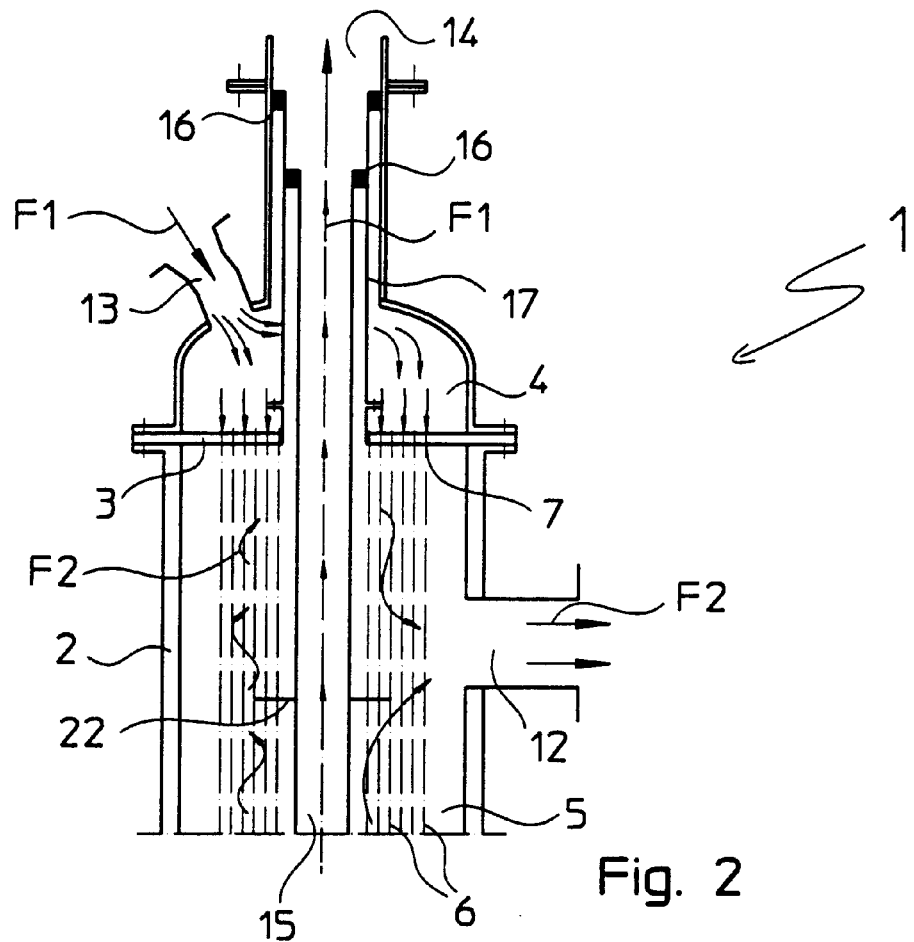
FIG. 2 shows a longitudinal cross section view of a part of the apparatus of FIG. 1, modified in accordance with a preferred embodiment of the present invention.
Figure 3:
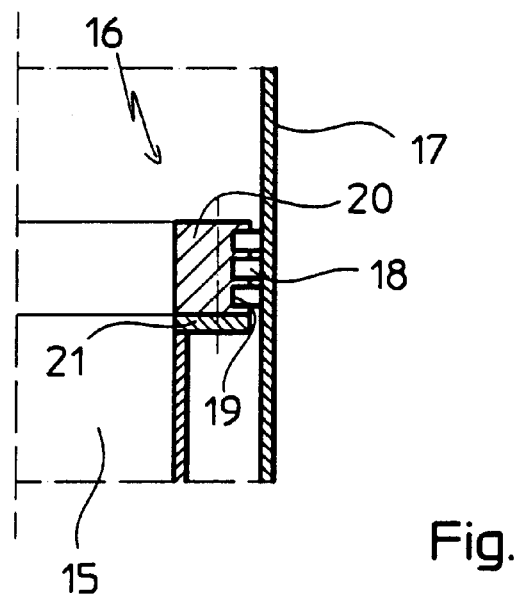
FIG. 3 shows a longitudinal cross section view in enlarged scale of a detail of the apparatus of FIG. 2.

With reference to FIGS. 1–3, reference number 1 indicates as a whole a reforming apparatus according to the present invention for the reforming reaction of a gaseous flow comprising methane and steam.

The apparatus 1 comprises a substantially cylindrical external shell 2 in which extends over the entire cross section thereof a tube plate 3 dividing the shell 2 in an indirect heat exchange feeding zone 5 and a zone 4 for feeding a gaseous flow comprising methane and steam to the zone 5.

A plurality of floating heat tubes, all indicated by reference number 6, extend longitudinally in the indirect heat exchange zone 5 from the tube plate 3.

The tubes 6 define within them a zone (not shown) for housing a reforming catalyst of known type. In addition, the tubes 6 have a first end 7 in fluid communication with the feeding zone 4 and a second end 8 in fluid communication with a chamber 9 for collecting a gaseous flow comprising $CO$, $CO_2$, and $H_2$ obtained from the reforming reaction. Reference number 10 indicates a tube plate arranged between the tubes 6 and the chamber 9, in the second end 8.

The shell 2 is also equipped—in the indirect heat exchange zone 5—with openings 11 and 12 which are respectively for inlet and outlet of a heating gas as heat source for the reforming reaction.

Openings 13 and 14 are also defined in the shell 2 at feeding zone 4, respectively for inlet of the reaction gas comprising methane and steam and outlet of the reacted gas comprising $CO$, $CO_2$, and $H_2$.

Advantageously, extraction duct 15 is provided in the shell 2 for extracting from the apparatus 1 the reacted gas. The extraction duct 15 is in fluid communication with the chamber 9 and the gas outlet opening 14.

Thanks to the particular structure resulting from the presence of a plurality of individual tubes 6 in combination with the chamber 9 and the reacted gas extraction duct 15, it is possible to secure an apparatus which is mechanically very simple and easy to implement as regards construction and which is at the same time extremely reliable and effective from the energy and reforming reaction conversion yield viewpoint.

In the example of FIG. 1, the extraction duct 15 is arranged coaxially with the shell 2 and extends parallel to the tubes 6 through the indirect heat exchange zone 5 and the feeding zone 4.

According to an alternative embodiment of the present invention (not shown), the extraction duct 15 extends from the chamber 9 to the lower end of the apparatus 1, and the outlet 14 is defined coaxially with and at the lower end of the shell 2.

With respect to the example of FIG. 1, it is possible in this manner to increase in the zone 5 the useful space for arrangement of the tubes 6 with resulting increase of the heat exchange surface.

Reference number 16 indicates generally gas sealing means for avoiding undesired by-pass of the reaction gas or reacted gas. The gas sealing means 16 also permit the different thermal expansions, in particular of the tubes 6 and the duct 15, so as to ensure optimal and reliable operation of the apparatus 1.

The gas sealing means 16 are arranged, with reference to FIG. 1, between the extraction duct 15 and the tube plate 3 and between the extraction duct 15 and the shell 2, while in the example of FIG. 2 they are arranged between the extraction duct 15 and the tube plate 3 and between the tube plate 3 and the shell 2.

According to the embodiment of FIG. 1, the gas sealing means 16 are advantageously all arranged in relation to a single part of the apparatus 1, i.e. the extraction duct 15, to simplify the arrangement of these means inside the apparatus as much as possible.

To facilitate maintenance operations of the gas sealing means 16, the latter can be arranged near the reacted gas outlet opening 14 as shown in FIG. 2.

According to this preferred embodiment of the present invention, the gas sealing means 16 are arranged in relation to a tubular appendage 17 of the tube plate 3 extending from the latter towards the opening 14.

Advantageously, the gas sealing means 16 are of the labyrinth type or of the compression ring type and preferably of the compression ring type.

In the description given below, the term: "labyrinth sealing means" is understood to mean a seal created by the coupling of two parts of generally tubular shape, a male part and female part, with the first having its external surface indented so that, once coupled, there are created solid ridges and empty spaces (labyrinth) between the coupled parts which prevent gas passage.

In the description given below, the term: "compression ring sealing means" is understood to mean a seal created by a compression ring arranged between a coupled male part and female part to prevent gas passage.

Thanks to this type of sealing means 16, it is possible to ensure gas seal and permit reliable and lasting expansion compensation even for continuous, large expansion rates as in the case of reforming apparatus.

FIG. 3 shows in enlarged scale a detail of the reforming apparatus 1 of FIG. 2 making clear the gas sealing means 16 of the compression ring type between the extraction duct 15 and the tubular appendage 17 of the tube plate 3.

The sealing means 16 comprise a plurality of compression rings 18 (preferably at least two), housed in respective cavities 19 of a cylindrical element 20 affixed to the end 21 of the extraction duct 15 preferably in a removable manner, e.g. by means of bolts (not shown).

The presence of the compression rings 18 between the duct 15 (male) and the tubular appendage 17 (female) prevents passage of reacted gas into the heat exchange zone 5 and at the same time permits the duct 15 to run along the tubular appendage 17 to compensate expansion thereof.

The gas sealing means 16 of the reforming apparatus 1 in the examples of FIGS. 1 and 2 are preferably of the type shown in FIG. 3.

With respect to the labyrinth seal, use of compression rings permits a series of advantages among which it is worthwhile mentioning: a more effective gas seal (less gas by-pass through the seal), greater structural flexibility (the gap between male and female can be up to 10 times greater than with labyrinth seals), and greater compactness of the sealing means (shorter for equal seal).

This means that the piston-ring sealing means can ensure good gas seal even in case of impairment and/or misalignment of the male and female parts, as well as greater flexibility during assembly and adjustment operations on the reforming apparatus 1, less sensitivity to the entry of foreign bodies and less seizure risk.

The use of piston-ring sealing means extends advantageously to an apparatus for carrying out endothermic or exothermic chemical reactions in general, e.g. even to ammonia or methanol synthesis reactors, to ensure gas seal between structurally distinct parts having different thermal expansion rates.

In FIGS. 1 and 2, the arrows F1 and F2 indicate the various paths taken in the reforming apparatus 1 by the gaseous flow comprising methane and steam (reaction gas) and by the hot gas flow for indirect heat exchange respectively.

Operation of the reforming apparatus according to the present invention is described herebelow.

The operating conditions of temperature indicated in the present description are for a primary reforming apparatus.

With reference to FIG. 1, a gaseous flow F1 comprising methane and steam (reaction gas), preheated to a temperature between 300° C. and 500° C. is fed to the feeding zone 4 of the apparatus 1 through the gas inlet opening 13 and made to pass into the tubes 6 (tube side) for the reforming reaction at a temperature between 500° C. and 1000° C. For this purpose, the tubes 6 are appropriately filled with catalyst.

The reforming reaction is made possible thanks to the heat transmitted by a hot gas flow F2 having a temperature between 900° C. and 1100° C. fed to the heat exchange zone 5 through the gas inlet opening 11. The hot gas flow F2 flows outside the tubes 6 (shell side) and is discharged from the shell 2 through the gas outlet opening 12 at a temperature between 300° C. and 600° C.

In particular, the hot gas flow F2 transmits the reaction heat by indirect heat exchange to the colder reaction gas flow F1.

The gaseous flow F1 comprising CO, $CO_2$, and $H_2$ obtained from the reforming reaction is discharged from the tubes 6 through the end 8, is collected in the chamber 9 and extracted from the apparatus 1 through the duct 15 and the gas outlet opening 14 at a temperature between 500° C. and 1000° C.

As set forth above, the gaseous flow F1, once collected and fed into the duct 15, is no longer in thermal connection with the reaction gas passing through the tubes 6 and thus there is advantageously avoided undesired heat exchange between the reacted gas and the reaction gas.

In addition, the expansion rates of the various parts of the apparatus 1—especially of the tubes 6 and the duct 15—due to the different materials and thermal stress to which they are subjected, are effectively compensated by the particular structure of the chamber 9 and the duct 15 and by the arrangement of the sealing means 16, which permit movement of the various parts and at the same time prevent undesired gas leakage.

It is important to note that the use of these sealing means does not negatively influence the construction simplicity of the apparatus according to the present invention.

In the examples of FIGS. 1 and 2, the tubes 6 are advantageously arranged in a tube bundle so as to optimize the occupation rate of the heat exchange zone 5.

In addition, to increase the surface area available and thus improve heat exchange, the tube bundle is preferably equipped with appropriate diaphragms 22 and the tubes 6 have fins (not shown).

For an ammonia synthesis process, the hot gas flow F2 comprises preferably the gaseous flow coming from the secondary reforming section.

From the foregoing, the numerous advantages achieved by the present invention are clear, in particular that of obtaining a reliable reforming apparatus which is structurally simple and easy to construct and which allows methane reforming with low energy consumption and operating and maintenance costs.

What is claimed is:

1. Reforming apparatus for the conversion of methane and steam into CO, $CO_2$ and $H_2$ comprising:

a substantially cylindrical external shell in which are defined an indirect heat exchange zone and a feeding zone for feeding a gaseous flow comprising methane and steam to the indirect heat exchange zone;

an opening formed in said shell for feeding in said indirect heat exchange zone a heating gas flow as heat source for said conversion, characterized in that it also comprises:

a plurality of floating head tubes containing a reforming catalyst extending longitudinally in said indirect heat exchange zone and in fluid communication with said feeding zone;

a chamber for collecting a gaseous flow comprising CO, $CO_2$ and $H_2$ obtained from said conversion and positioned downstream of said tubes and directly connected thereto;

an extraction duct open in said collection chamber for extracting from the shell said gaseous flow comprising CO, $CO_2$ and $H_2$, said extraction duct being arranged coaxially with said shell and extending parallel to said tubes through said indirect heat exchange zone and said feeding zone from said collection chamber to a gas outlet opening from said shell; and gas sealing means between said duct and a tube plate positioned between said feeding zone and said indirect heat exchange zone, said gas sealing means permitting movement of said duct and at the same time preventing gas leakage.

2. Apparatus according to claim 1, characterized in that there are provided gas sealing means between said duct and said shell, said gas sealing means permitting movement of said duct while preventing gas leakage.

3. Apparatus according to claim 1, characterized in that there are provide gas sealing means between said tube plate and said shell, said gas sealing means permitting movement of said tube plate while preventing gas leakage.

4. Apparatus according to claim 2, characterized in that said gas sealing means between said duct and said shell are arranged adjacent said outlet opening.

5. Apparatus according to claim 1, characterized in that said gas sealing means are comprised of at least one compression ring.

6. Apparatus according to claim 3, characterized in that said gas sealing means between said tube plate and said shell are arranged adjacent said outlet opening.

* * * * *